US00PP08875P

United States Patent [19]

Tvrtkovic-Sahin et al.

[11] Patent Number: Plant 8,875

[45] Date of Patent: Aug. 30, 1994

[54] ASTER PLANT NAMED CASABLANCA

[75] Inventors: Zelimir K. Tvrtkovic-Sahin, Alphen aan den Rijn; Petrus J. Akerboom, Ter Aar, both of Netherlands

[73] Assignee: DeNachtvlinder B.V., Paradijsweg, Netherlands

[21] Appl. No.: 7,236

[22] Filed: Jan. 21, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Foley & Lardner

[57] ABSTRACT

A distinct cultivar of aster plant named Casablanca, particularly characterized by its cupped capitulum form; daisy capitulum type with strong petals; white ray floret color; diameter across face of capitulum of 34 to 35 mm at maturity; strong, well branched flower stems; strong leaves, with low susceptibility to yellowing, and good tolerance to foliage diseases.

2 Drawing Sheets

The present invention comprises a new and distinct cultivar of Aster plant, hereinafter referred to by the cultivar name Casablanca.

Casablanca is a product of a planned breeding program which had the objective of creating new perennial Aster cultivars for year-round commercial production having well branched flower stems, good flower size, good flower form, and having superior lasting quality of the cut flowers. Such traits in combination were not present or needed improvement in previously available commercial cultivars.

Casablanca was originated from a hybridization made by the inventors K. Sahin and P. Akerboom in a controlled breeding program in Ter Aar, The Netherlands, in 1984. The felame parent of Casablanca was *Aster pringlie* c.v. Monte Casino. The male parent was an unnamed *Aster novi-belgii* seedling.

Casablanca was discovered and selected as one flowering plant within the progeny of the stated parentage by the inventors K. Sahin and P. Akerboom on Sep. 2, 1985 in a controlled environment in Ter Aar.

The first act of asexual reproduction of Casablanca was accomplished when vegetative cuttings were taken from the initial selection in November 1985 in a controlled environment in Ter Aar, by a technician working under formulations established and supervised by K. Sahin and P. Akerboom.

Horticultural examination of selected units initiated in 1985 and 1986 has demonstrated that the unique combination of characteristics as herein disclosed for Casablanca are firmly and are retained through successive generations of asexual reproduction.

Casablanca has not been observed under all possible environmental conditions. The phenotype may vary significantly with variations in environment such as temperature, light intensity and daylength, without, however, any variation in genotype.

The following observations, measurements and comparisons describe plants grown in Ter Aar under greenhouse conditions which approximate those generally used in commercial greenhouse practice in The Netherlands.

The following traits have been repeatedly observed and are determined to be basic characteristics of Casablanca, which, in combination, distinguish this Aster as a new and distinct cultivar:

1. Cupped capitulum form.

2. Daisy capitulum type, with strong petals.
3. White ray floret color.
4. Diameter across face of capitulum of 34 to 35 mm at maturity.
5. Strong, well branched flower stems.
6. Strong leaves, with low susceptibility to yellowing.
7. Good tolerance to foliage diseases.
8. Can be grown as a garden perennial or as a forced greenhouse cultivar. When forced, it will flower as many as three times a year.

In the accompanying color photographic drawings, the photograph on sheet 1 comprises a front view of a typical plant of Casablanca in bloom and bud.

The photograph on sheet 2 comprises a closeup view showing the flowers in much greater detail.

Of the commercial cultivars known to the inventors, the most similar to Casablanca is White Butterfly, disclosed in the inventors' U.S. Plant Pat. No. 7,397. The cultivar White Butterfly is a sibling of Casablanca, both being progeny of the cross described above. Compared to White Butterfly, Casablanca has better flower shape and stronger petals, its leaves are stronger and less susceptible to yellowing, known as aster yellows, it has stronger stems, and Casablanca is less susceptible to foliage diseases. Both cultivars have white flowers and are similar to each other in other characteristics, for example, keeping quality or vaselife when utilized for cut flowers.

In the following description color references are made to The Royal Horticultural Society Colour Chart. The color values were determined at Alphen aan den Rijn, The Netherlands.

Classification:

*Botanical.*—*Aster pringlei*×*novi-belgii* cv Casablanca.

*Commercial.*—Small daisy-like spray Aster, greenhouse or garden perennial.

INFLORESCENCE

A. Capitulum:

*Form.*—Cupped.

*Type.*—Daisy.

*Diameter across face.*—31–33 mm.

*Arrangement.*—Raceme inflorescence each branch.

B. Corolla of ray florets:

*Color (general tonality from a distance of three meters).*—White.

*Color (upper surface).*—Whiter than 155B.

*Color (under surface).*—Whiter than 155B.

*Shape of floret.*—Apex reflexing; narrow, oblong, straight.

*Size of floret.*—17–18 mm long×2.5 mm wide.

*Number of ray florets.*—34–68.

C. Corolla of disc florets:

*Color (mature).*—154C.

*Color (immature).*—154A.

*Diameter of disc.*—7 mm.

D. Reproductive organs:

*Androecium.*—Present on disc florets only; no pollen.

*Gynoceium.*—Present on both ray and disc florets.

E. Buds:

*Size.*—Just prior to opening, approximately 7 mm.

*Color.*—Immature 154A, mature just prior to opening 154C.

THE PLANT

A. General appearance:

*Height.*—Medium to tall, depending on light. Under continuous long days it can grow up to 2 meters tall; medium branching.

B. Foliage:

*Color.*—137A, with low susceptibility to yellowing.

*Shape.*—Oblanceolate and linear, with occasional downward reflexing at the tip.

*Size.*—For bottom leaf of stem, length approximately 155 to 167 mm and width approximately 21 to 24 mm; fifth leaf from top of stem, length approximately 25 mm and width approximately 3 mm.

*Margin.*—Entire.

*Arrangement.*—Alternate, with angle acute; leaves are strong.

C. Disease resistance: Casablanca has proved to be much less susceptible to foliage diseases than its sibling White Butterfly.

D. Fertility: The new cultivar is fertile and has been used in breeding as a female.

We claim:

1. A new and distinct Aster plant named Casablanca, as described and illustrated.

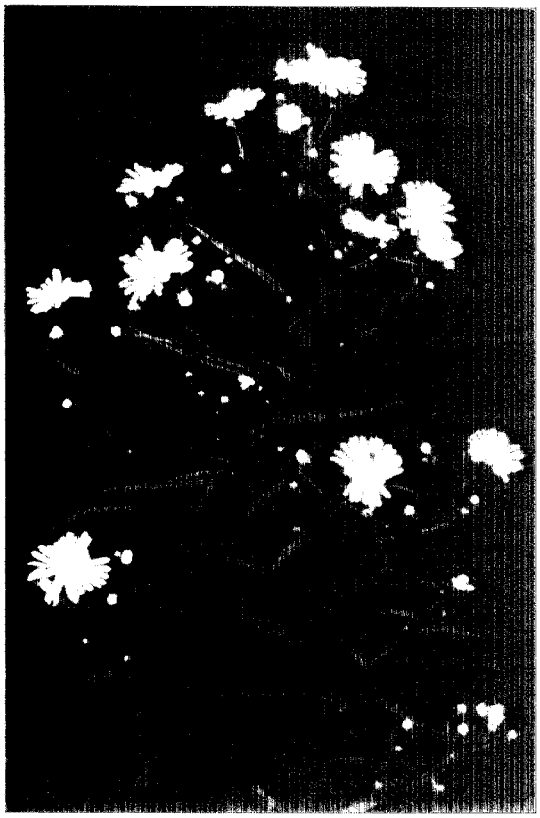

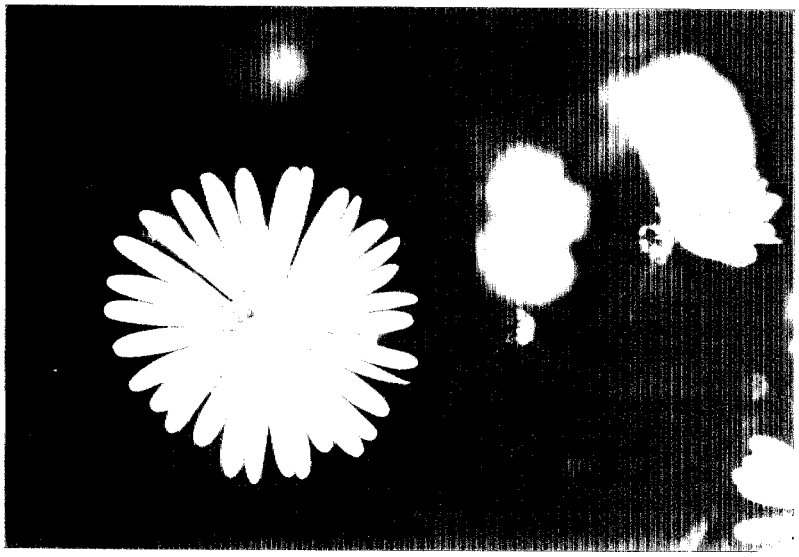

* * * * *